(12) United States Patent
Dorawa et al.

(10) Patent No.: US 9,259,242 B2
(45) Date of Patent: *Feb. 16, 2016

(54) FIXATION CLAMP

(71) Applicant: Stryker Trauma SA, Selzach (CH)

(72) Inventors: Klaus Dorawa, Schoenkirchen (DE); Axel Bernhard Cremer, Lommiswil (CH); Adam Busch, Olten (CH)

(73) Assignee: Stryker Trauma SA (CH)

( * ) Notice: Subject to any disclaimer, the term of this patent is extended or adjusted under 35 U.S.C. 154(b) by 45 days.

This patent is subject to a terminal disclaimer.

(21) Appl. No.: 14/175,376

(22) Filed: Feb. 7, 2014

(65) Prior Publication Data

US 2014/0155894 A1 Jun. 5, 2014

Related U.S. Application Data

(63) Continuation of application No. 13/302,689, filed on Nov. 22, 2011, now Pat. No. 8,685,023.

(30) Foreign Application Priority Data

Dec. 14, 2010 (EP) .................................... 10194943

(51) Int. Cl.
*A61B 17/64* (2006.01)

(52) U.S. Cl.
CPC ......... *A61B 17/6466* (2013.01); *A61B 17/6416* (2013.01)

(58) Field of Classification Search
CPC .................. A61B 17/6466; A61B 17/6416
USPC ............ 606/53–59; 600/227; 403/322.4, 377, 403/385, 344, 384, 289
See application file for complete search history.

(56) References Cited

U.S. PATENT DOCUMENTS

| 2,250,417 A | 7/1941 | Ettinger |
|---|---|---|
| D228,970 S | 10/1973 | Cohen |

(Continued)

FOREIGN PATENT DOCUMENTS

| CH | 657899 A5 | 9/1986 |
|---|---|---|
| DE | 518329 C | 2/1931 |

(Continued)

OTHER PUBLICATIONS

European Search Report for EP 10194943.6 dated Feb. 23, 2011.

(Continued)

*Primary Examiner* — Pedro Philogene
(74) *Attorney, Agent, or Firm* — Lerner, David, Littenberg, Krumholz & Mentlik, LLP

(57) ABSTRACT

A fixation clamp is used in an external fixation system for holding bone fragments adjacent to each other with the help of fixation elements. The clamp has at least one clamping assembly having at least one reception to accommodate a fixation element along the longitudinal axis of the reception and at least one locking element extending through the clamping assemblies for blocking the position of the clamping assemblies in a defined angular position. Between the locking element and the at least one clamping assembly there is arranged a washer. The clamping assembly comprises a first contact surface and the washer comprises a second contact surface wherein the first contact surface is in contact with the second contact surface. The washer has a through bore and an opening extending radially from the bore to an outer surface of the washer.

21 Claims, 3 Drawing Sheets

(56) References Cited

U.S. PATENT DOCUMENTS

| | | |
|---|---|---|
| D237,631 S | 11/1975 | Katzman |
| D255,713 S | 7/1980 | Sturges |
| D282,962 S | 3/1986 | Gerber |
| D283,725 S | 5/1986 | Mahoney |
| 4,620,533 A | 11/1986 | Mears |
| 4,662,365 A | 5/1987 | Gotzen et al. |
| D301,496 S | 6/1989 | Yonesawa et al. |
| 5,071,437 A | 12/1991 | Steffee |
| 5,098,432 A | 3/1992 | Wagenknecht |
| 5,152,280 A | 10/1992 | Danieli |
| 5,281,222 A * | 1/1994 | Allard et al. .............. 606/54 |
| 5,304,177 A | 4/1994 | Pennig |
| 5,376,091 A | 12/1994 | Hotchkiss et al. |
| 5,429,637 A | 7/1995 | Hardy |
| 5,443,465 A | 8/1995 | Pennig |
| 5,630,815 A | 5/1997 | Pohl et al. |
| D380,262 S | 6/1997 | Van Funderburk et al. |
| 5,662,648 A | 9/1997 | Faccioli et al. |
| 5,746,741 A | 5/1998 | Kraus et al. |
| 5,752,954 A | 5/1998 | Mata et al. |
| 5,827,282 A | 10/1998 | Pennig |
| 5,846,245 A | 12/1998 | McCarthy et al. |
| 5,891,144 A | 4/1999 | Mata et al. |
| 5,921,985 A | 7/1999 | Ross, Jr. et al. |
| 6,019,769 A | 2/2000 | McCarthy et al. |
| 6,024,745 A | 2/2000 | Faccioli et al. |
| 6,080,153 A | 6/2000 | Mata et al. |
| D429,334 S | 8/2000 | Solem |
| 6,217,577 B1 | 4/2001 | Hofmann |
| 6,308,598 B1 | 10/2001 | O'Neil |
| D455,831 S | 4/2002 | Koros et al. |
| 6,386,786 B1 | 5/2002 | Perlman et al. |
| 6,409,729 B1 | 6/2002 | Martinelli et al. |
| 6,482,206 B2 | 11/2002 | Schoenefeld |
| 6,520,962 B1 | 2/2003 | Taylor et al. |
| 6,565,564 B2 | 5/2003 | Hoffman et al. |
| 6,613,049 B2 * | 9/2003 | Winquist et al. .............. 606/59 |
| 6,616,664 B2 | 9/2003 | Walulik et al. |
| 6,652,523 B1 | 11/2003 | Evrard et al. |
| D483,642 S | 12/2003 | Lin |
| 6,702,814 B2 | 3/2004 | Walulik et al. |
| D493,225 S | 7/2004 | Varga et al. |
| D494,274 S | 8/2004 | Varga et al. |
| D501,555 S | 2/2005 | Varga et al. |
| 6,916,319 B2 | 7/2005 | Munting |
| 7,004,943 B2 | 2/2006 | Ferrante et al. |
| 7,048,735 B2 | 5/2006 | Ferrante et al. |
| D526,410 S | 8/2006 | Phillips et al. |
| D532,277 S | 11/2006 | Shih |
| D537,939 S | 3/2007 | Phillips et al. |
| 7,261,713 B2 | 8/2007 | Langmaid et al. |
| D551,763 S | 9/2007 | Phillips et al. |
| 7,282,052 B2 | 10/2007 | Mullaney |
| D556,899 S | 12/2007 | Veliss et al. |
| D558,337 S | 12/2007 | Jones et al. |
| 7,449,023 B2 | 11/2008 | Walulik et al. |
| 7,479,142 B2 | 1/2009 | Weiner et al. |
| 7,491,008 B2 * | 2/2009 | Thomke et al. .............. 403/373 |
| 7,527,626 B2 | 5/2009 | Lutz et al. |
| 7,562,855 B2 | 7/2009 | Oetlinger |
| 7,588,571 B2 | 9/2009 | Olsen |
| 7,618,417 B2 | 11/2009 | Thomke et al. |
| D607,102 S | 12/2009 | Robinson |
| 7,749,224 B2 | 7/2010 | Cresina et al. |
| 7,806,623 B2 * | 10/2010 | Thomke et al. .............. 403/385 |
| D632,791 S | 2/2011 | Murner |
| D633,206 S | 2/2011 | Murner |
| D633,207 S | 2/2011 | Murner |
| D633,208 S | 2/2011 | Murner |
| 8,172,840 B2 | 5/2012 | Murner et al. |
| D663,030 S | 7/2012 | Murner et al. |
| 2001/0049526 A1 | 12/2001 | Venturini et al. |
| 2002/0037193 A1 | 3/2002 | Gibbons et al. |
| 2002/0077629 A1 | 6/2002 | Hoffman et al. |
| 2003/0199738 A1 | 10/2003 | Yager |
| 2004/0044344 A1 | 3/2004 | Winquist et al. |
| 2004/0059331 A1 | 3/2004 | Mullaney |
| 2005/0203520 A1 | 9/2005 | Volzow |
| 2005/0240265 A1 | 10/2005 | Kuiper et al. |
| 2006/0025703 A1 | 2/2006 | Miles et al. |
| 2006/0039750 A1 | 2/2006 | Thomke et al. |
| 2006/0052785 A1 | 3/2006 | Augostino et al. |
| 2006/0155276 A1 | 7/2006 | Walulik et al. |
| 2006/0167453 A1 | 7/2006 | Hoffmann-Clair et al. |
| 2006/0287652 A1 | 12/2006 | Lessig et al. |
| 2007/0038217 A1 | 2/2007 | Brown et al. |
| 2007/0123856 A1 | 5/2007 | Deffenbaugh et al. |
| 2007/0198012 A1 | 8/2007 | Thomke et al. |
| 2007/0233061 A1 | 10/2007 | Lehmann et al. |
| 2008/0065068 A1 | 3/2008 | Thomke et al. |
| 2008/0215053 A1 | 9/2008 | Thomke et al. |
| 2008/0306527 A1 | 12/2008 | Winslow et al. |
| 2008/0306528 A1 | 12/2008 | Winslow et al. |
| 2009/0018541 A1 * | 1/2009 | Lavi .............. 606/59 |
| 2009/0088751 A1 | 4/2009 | Mullaney |
| 2009/0099565 A1 | 4/2009 | Weiner et al. |
| 2009/0299368 A1 * | 12/2009 | Bauer .............. 606/57 |
| 2009/0306661 A1 | 12/2009 | Thomke et al. |
| 2009/0326532 A1 | 12/2009 | Schulze |
| 2010/0298827 A1 | 11/2010 | Cremer et al. |
| 2011/0066151 A1 | 3/2011 | Murner et al. |
| 2011/0087226 A1 | 4/2011 | Murner et al. |
| 2012/0004659 A1 | 1/2012 | Miller et al. |
| 2012/0150181 A1 | 6/2012 | Dorawa et al. |
| 2012/0150182 A1 | 6/2012 | Dominik et al. |

FOREIGN PATENT DOCUMENTS

| | | |
|---|---|---|
| DE | 10246418 A1 | 4/2004 |
| EP | 314021 A2 | 5/1989 |
| EP | 0700664 A1 | 3/1996 |
| EP | 2250968 A1 | 11/2010 |
| FR | 2787697 A1 | 6/2000 |
| JP | H10078019 | 3/1998 |
| JP | 2000009128 A | 1/2000 |
| JP | 2003325058 A | 11/2003 |
| WO | 0156486 A1 | 8/2001 |
| WO | 2006116307 | 11/2006 |
| WO | 2007001945 A1 | 1/2007 |

OTHER PUBLICATIONS

European Search report for EP 10194944.4 dated Feb. 23, 2011.
European Search Report for EP 10194945.1 dated Feb. 25, 2011.
http://emedicine.medscape.com/article/1982756-overview searched RMS Jan. 15, 2013.
http://www.smith-nephew.com/us/professional/products/all-products/jet-x/ searched RMS Jan. 15, 2013.

* cited by examiner

FIXATION CLAMP

CROSS-REFERENCE TO RELATED APPLICATION

This application is a continuation of U.S. application Ser. No. 13/302,689 filed Nov. 22, 2011 and claims priority from European Patent Application No. 10 194 943.6 filed Dec. 14, 2010, the disclosures of which are hereby incorporated herein by reference.

BACKGROUND OF THE INVENTION

The present invention relates to a fixation clamp and, more particularly, to a fixation clamp for use in an external fixation system for holding bone fragments adjacent to each other.

External fixation systems are widely used to connect two or more bone fragments to each other. Such systems comprise bone screws, pins, wires which are inserted directly into the bone material and these systems use external structural elements as fixation rods, bars and rings. In order to connect the rods and bars to form a rigid frame, fixation clamps are used. Furthermore, fixation clamps are used to connect this screws and pins to the rigid frame to specifically hold bone fragments at an intended place.

One adjustable fixation clamp is known from U.S. Pat. No. 6,080,153 comprising two pairs of jaws allowing clamping of a rod as well as of a pin.

A clamp for multiple rod-shaped elements is known from U.S. Pat. No. 7,618,417 having one single pair of jaws. However, such a clamp allows clamping more than two, e.g. three or four rod-shaped elements as pins with one single clamp, thus reducing the number of clamps. However, one further fixation clamp is necessary to fix the rod of said clamp to the frame of the fixation system.

U.S. Patent Application Publication No. 2006/0287652 mentions that usual fixation clamps as e.g. known from U.S. Pat. No. 6,080,153 allow clamping of one single screw or pin to the frame and that this way to attach pins or rods leads to bulky fixation systems. Therefore this publication discloses a fixation clamp addressing this problem and comprises two pairs of jaws within which each pair of jaws allows the introduction and clamping of two rods or pins etc. at the same time.

These clamps according to the prior art either provide different diameters of the receptions provided by the jaws to introduce different sizes of rods, pins or wires, or they rely on additional inserts as e.g. disclosed in U.S. Patent Application Publication No. 2008/0065068. Such inserts reduce the diameter of the reception cavities to allow a secure fixing of differently sized rods, pins or wires.

From U.S. Patent Application Publication No. 2010/0298827 a further fixation clamp is known. Users feel very comfortable with the fixation clamp according to this publication. However, there is a need to have a fixation clamp which can be cleaned more easily and which can also compensate angular orientation between the rods or pins during the mounting process.

BRIEF SUMMARY OF THE INVENTION

It is one aspect of the present invention to provide a fixation clamp which overcomes the disadvantages of prior art. It is in particular an object of the present invention to provide a fixation clamp which is adjustable during the mounting process to a larger degree.

Such an aspect is solved by the features of claim 1. Therefore a fixation clamp, more particularly for use in an external fixation system for holding bone fragments adjacent to each other with the help of fixation elements, comprises at least one clamping assembly having at least one reception to accommodate a fixation element along the longitudinal axis of the reception and at least one locking element extending through the clamping assemblies for blocking the position of the clamping assemblies in a defined angular position, wherein between the locking element and the at least one clamping assembly there is arranged a washer. The clamping assembly comprises a first contact surface which is at least partly spherical and convex and in that said washer comprises a second contact surface which is at least partly spherical and concave, wherein the first contact surface is in contact with the second contact surface. Due to the arrangement of the spherical concave and convex surface it is possible to provide the fixation clamp with better adjustment properties.

It is a further aspect of the present invention to provide a fixation clamp which is dismountable for cleaning purposes in a very easy manner. This aspect is achieved by the washer which is dismountable in a direction substantially perpendicular to the locking element.

In particular it shall be prevented that the fixation clamp has to be dismounted in a complicated manner and/or that all of the parts of the fixation clamps have to be separated. This object is achieved by an abutment surface. The bore comprises towards the contact surface preferably a first diameter which is adjoined by a second diameter, wherein the first diameter is larger than the second diameter such that between the first and the second diameter an abutment surface is provided, which abutment surface serves as abutment element for the locking element, in particular for flange, in case the washer is removed.

Further embodiments of the invention are set forth in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DETAILED DESCRIPTION

Figure 1:
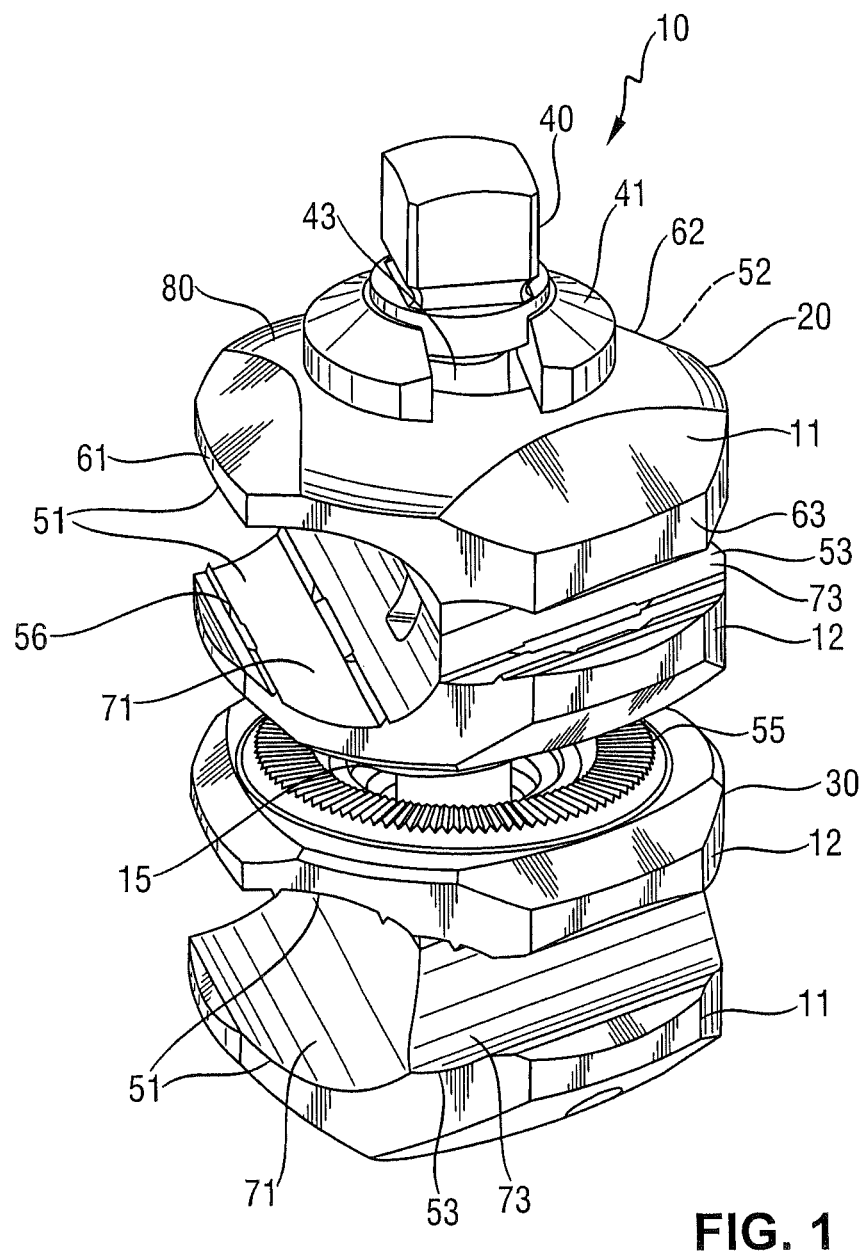
FIG. 1 shows a perspective view of a first embodiment of a fixation clamp of the present invention.
Figure 2:
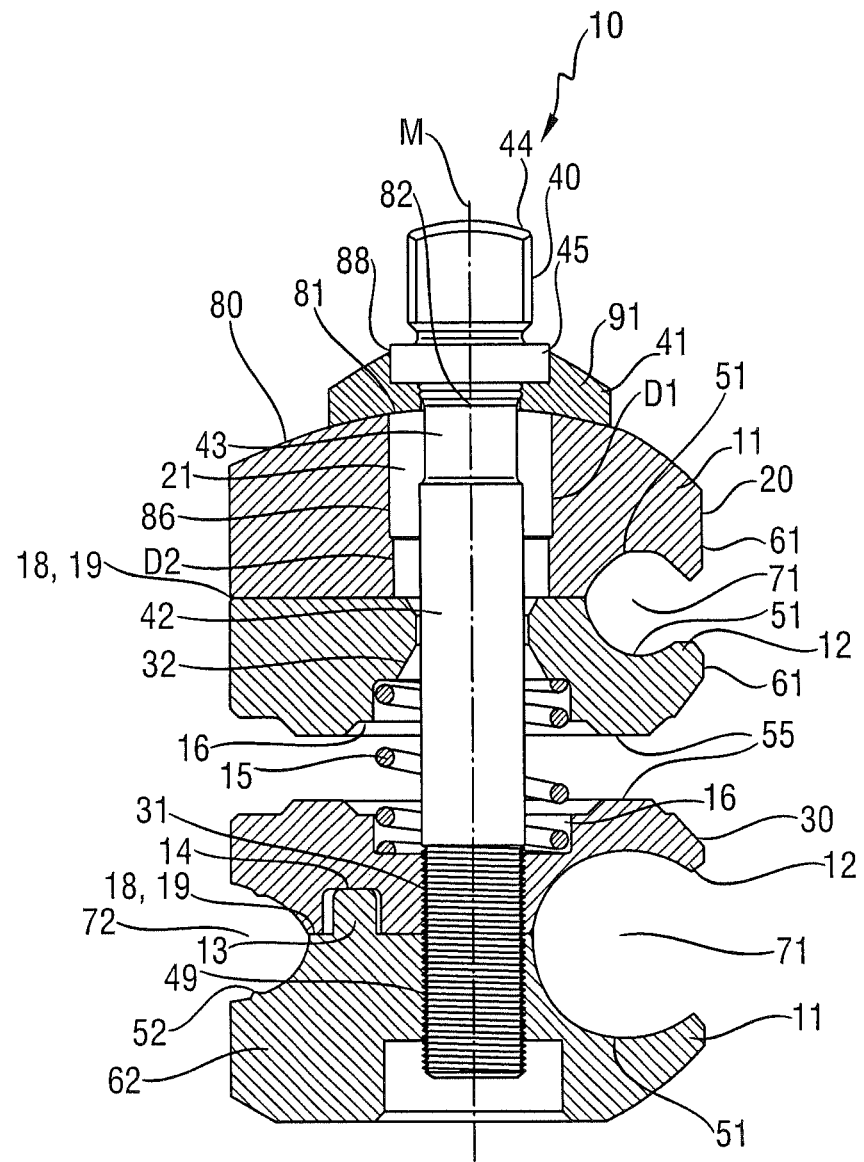
FIG. 2 shows a cross-section of the fixation clamp according to FIG. 1.

FIGS. 1 and 2 show a preferred first embodiment of a clamping element or fixation clamp 10 pursuant to the invention. The clamping element 10 consists of a first clamping assembly 20 and a second clamping assembly 30 and a locking element or shaft 40 which is positioned through bores 21, 31 within the two clamp assemblies 20, 30 along the longitudinal axis M of shaft 40. The shaft 40 is preferably a locking element adapted to allow closing the clamp assemblies 20 and 30. Shaft 40 enters a first jaw 11 through a washer 41.

The shaft 40 comprises a head portion 44, a reduced diameter portion 43 which is followed by a shaft portion 42 and a thread portion 49. The outer threaded portion 49 is adapted to be screwed into a complementary inner thread within the distal jaw so that turning the head of the shaft 40 changes the longitudinal position of the shaft 40 against the lower jaw 11, which allows opening or closing the entire clamp 10 against the force of a spring 15 provided between the two clamp assemblies 20 and 30. Spring 15 is preferably positioned in corresponding receptions 16 in the jaws 12. Instead of a spring 15, provided around shaft 40, it is possible to provide a different spring means as Belleville washers or an elastic compressible solid or foam. Upon closing of the clamp assemblies 20 and 30 the jaws 12 adjacent to spring 15 can eventually come into contact and then the anti-rotation surfaced 55 which are provided in both surfaces of the jaws 12 fix the angular orientation of each clamping assembly 20 and 30 against the other.

Preferably after having mounted the shaft 40 with the thread 49 within the lower jaw 11, the end portion of the thread is destroyed through pressure to ensure that the shaft 40 cannot be removed from the clamping assemblies 20, 30 to maintain the clamp as one single piece.

Each clamping assembly 20 or 30 comprises two opposing clamping jaws 11 and 12. These jaws 11 and 12 are essentially similarly shaped on the sides facing each other. Each of the jaws 12, 11 comprises a respective contact surface 18, 19 facing the other surface of the jaw 11, 12.

In order to prevent rotation between the jaw 11 and the jaw 12 as well as in order to prevent a misalignment of the jaw 11, 12 at least one orientation device 13, 14 is arranged on the surfaces 18, 19. In the present embodiment in the second clamping assembly 30 the jaw 11 comprises an opening 14 extending into surface 18 and the jaw 12 comprises a pin 13 extending from surface 19. The pin 13 extends into the opening 14. This pin-opening connection prevents therefore a possible rotation between the jaws 11, 12 and a possible misalignment between the jaws 11, 12.

The jaws 11 and 12 are provided here with three grooves 51, 52 and 53. Grooves 51, 52 and 53 are all provided in a same plane perpendicular to the longitudinal axis of shaft 40. In that plane they are oriented perpendicular to the radial direction from the center of the bore 21 or 31. As such the grooves 51, 52 and 53 are substantially parallel to outer side wall 61, 62 or 63 of each pair of jaws 11 and 12.

Each pair of grooves 51, 52 or 53, respectively, in each jaw 11 and 12, define one reception, i.e. a first reception 71, a second reception 72 and a third reception 73. The grooves 51, 52 and 53 are each formed as a rounded semi-spherical recess in section to provide receptions 71, 72 and 73 which accommodate cylindrical pins or rods with a defined diameter, if the clamp is closed. The outer side walls 61, 62 or 63 can comprise an inclined sliding surface to allow an easier clipping of such pins or rods 100 into the corresponding reception. The grooves 51, 52, are called to form rounded semi-spherical recesses in a section. This means that the recesses provided by the grooves 51, 52, 53 have a hollow cylindrical shape to accommodate rod-shaped elements. Some or all of the grooves 51, 52, and 53 are also provided with friction enhancing elements such as ribs 56.

All three grooves 51, 52 and 53 have different sizes so that the corresponding receptions 71, 72 and 73 have three different sizes. In other words each reception 71, 72 or 73 is adapted to accept a different fixation element, i.e. a rod, screw, pin or wire having a different diameter. One preferred embodiment of the first clamping assembly 20 has grooves to accept fixation elements having a diameter of 12 mm, 8 mm and 5 mm, respectively. A different embodiment may have a sequence of diameters of 8 mm, 6 mm and 4 mm, respectively.

The second clamping assembly 30 according to the embodiment of FIG. 1 also comprises two jaw portions 11 and 12 and these comprise three grooves 51, 52, 53. These grooves 51, 52, 53 also comprise a sequence of different sizes.

In the embodiment shown the inner jaws portion 12 have an identical structure as have the outer jaws 11, especially in view of the anti-rotation device 55, the reception 16 for a spring 15.

Within a preferred embodiment the first clamping assembly 20 may comprise a sequence of smaller sizes, e.g. 7 mm, 5 mm and 3 mm; or 6 mm, 5 mm and 4 mm; and the second clamping assembly 30 may comprise a sequence of larger sizes, e.g. 13.5 mm, 12 mm and 10 mm. Different sizes are possible, usually for wires starting from 2 mm diameter until thicker rods with a diameter of 30 mm are used within such a clamp 10. Such a clamp allows using one single versatile clamp, wherein the first clamping assembly 20 is used to fix a specific pin or screw or wire having a diameter for which one of the receptions 71, 72 or 73 is adapted. The user takes the clamp 10 and orients the first clamping assembly 20 into the correct alignment so that the pin or screw can be clipped into the corresponding reception.

Then the clamp 10 can be clamped on a rod of an external fixator with the help of the second clamping assembly 30. Second clamping assembly 30 can be oriented in a way so that the rod can be clipped into the corresponding reception. It is an advantage of the clamp 10 having two clamping assemblies 20 and 30 according to the invention, that a practitioner attaching such a clamp at a bone screw with one clamping assembly 20 and subsequently a rod of an external fixator to the other clamping assembly 30 can check the robustness of his external fixator, and if he finds that the rod he has used is not stiff enough, he simply opens the second clamping assembly 30, removes the thinner rod, turns the second clamping assembly 30 e.g. 60 degrees into one direction or the other around the longitudinal axis to align the larger reception with the new thicker rod and replaces it. This change does not necessitate the replacement of the clamp 10 itself as necessary with prior art systems. The method to replace such a rod is faster and more reliable since the clamping of the bone screw is not changed, and avoids use of a second sterile clamp at said time.

It is of course also possible that the second clamping assembly 30 is a traditional clamping assembly or even any other element known in the prior art with clamping elements. The object of a versatile clamping assembly is already achieved through one first clamping assembly 20, since it allows clamping one of three different sizes of screws, pins of wires through simple reorientation of the first clamping assembly 20.

FIG. 2 shows a cross-section of the clamp according to FIG. 1, wherein the clamp 10 is shown in a premounted state, i.e. the spring 15 is under tension. The upper jaw 11 of the first clamping assembly 20 is therefore pushing the washer 41 against a flange 45 of the head of shaft 40. The bore 21 which accommodates part of the shaft portion 42 and the reduced diameter portion 43 is provided with a larger diameter than the respective diameter of the shaft 40 so that an angular or pivoting movement of the first clamping assembly 20 against the shaft 40 is possible. This is in particularly advantageous during the mounting process of the fixation clamp. With this regard it has to be noted that also bore 31 can be provided with a larger diameter than the respective section of the shaft 40 such that jaw 12 of the second clamping assembly becomes pivotable to the shaft 40.

The diameter D1, D2 of bore 21 of the first clamping assembly 20 is larger than the diameter of the locking element 40 extending through the bore 21. Thereby a pivoting movement or displacement between the locking element 40 and the first clamping assembly 20 during positioning the clamping assemblies 20, 30 and the pins or rods becomes possible. In the present embodiment the bore 21 in the first jaw 11 is a bore 21 having an abutment surface 86. The abutment surface 86 is provided by means a step-like bore 21 having a first section with a first diameter D1 and a second section with a second diameter D2. The first diameter D1 is larger than the second diameter D2. The abutment surface 86 serves as abutment element for the locking element 40 in particular for the flange 45 in case washer 41 is removed. Hence the abutment surface 86 together with the flange 45 prevents that the first clamping assembly 20 will be separated from the second clamping assembly 30 when the washer is removed. Particularly during a cleaning or sterilization process the prevention of such a separation is very advantageous.

Alternatively the bore 21 can be provided with a conical section 32 as shown with bore 21 in the jaw 12 of the first clamping assembly. In the present embodiment there are two conical sections arranged, whereby the diameter of the bore 21 decreases with increasing length of the bore as seen from outside of the jaw 12. In case two conical sections 32 are present the degree of the pivoting motion can be increased.

The shaft 40 as part of a locking element is threaded into the lower jaw 11 of the second clamping assembly 30. Hence the lower jaw 11 comprises a threaded opening. Threading may be provided in the bore or the screw may exhibit self-tapping threading. Quite generally, a locking element may be provided which may be a lever locking element or a bayonet lock. Among these locking elements may also be supporting disks or toothed disks, which, for the sake of simplicity, are not shown in the drawings.

Therefore the two clamp assemblies 20, 30 can be opened and closed through turning the head of shaft 40 and thus turning said shaft 40 in the jaw thread.

In the cross-sectional view of FIG. 2 it can also be seen that the locking element 40 extends through the first clamping assembly 20 and is in contact with the second clamping assembly 30 by means of the threaded portion 49. In mounting position in which the rods or pins will be positioned in the receptions 71, 72, 73 the first clamping assembly 20 is moveable along the middle axis M of the threaded portion 49. Upon actuation of the locking element 40 the first clamping assembly 20 will be moved against the spring pressure towards the second clamping assembly 30 such that the anti-rotation surface 55 of the first clamping assembly 20 comes into contact with the respective anti-rotation surface 55 of the second clamping assembly 30. Once the locking element 40 is firmly tightened the first clamping assembly 20 and the second clamping assembly 30 are in contact with each other via the anti-rotation surface 55.

In FIG. 2 the mounting position of clamping assemblies 20, 30 is shown. Thereby the clamping assemblies 20, 30 are positioned at the distance to each other with regard to the middle axis M. The second clamping assembly 20 is in contact with the locking element 40 and the spring 15 pushes the first clamping assembly away from the second clamping assembly 20 towards the washer 41 which is contact with the flange 45 of the locking element.

To summarize: The clamping assemblies 20, 30 will be moved due to actuation of the locking element 40 from a mounting position to a locking position and afterwards when fixation shall be cancelled from the locking position to the mounting position. After use the washer 41 will be removed as explained below in order to sterilize the clamping element 10 for further use.

Figure 3:
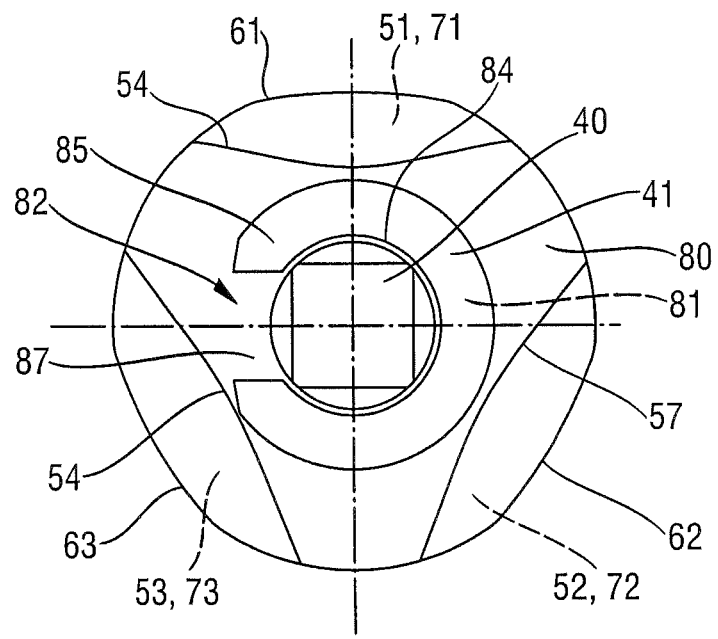
FIG. 3 shows a top view of the fixation clamp for FIG. 1.

FIG. 3 shows a view from above on the clamp according to FIGS. 1 and 2. Since the embodiment of FIG. 1 comprises three grooves 51, 52 and 53, there are three side walls 61, 62 and 63, which provide, when looked from above as in FIG. 2 a triangular shape of each clamping assembly 20 or 30.

In the present embodiment the first clamping assembly 20 here the jaw 11 comprises a first contact surface 80 which is in contact with a second contact surface 81 of the washer 41. The washer 41 and the first clamping assembly 20 are in contact via said contact surfaces 80, 81. The contact surfaces 80, 81 are spherical having the same curvature radius such that the washer is enabled to slide with respect to the first clamping assembly 20 on the contact surface 80 when it comes to the above mentioned pivoting motion of the first clamping assembly 20 with respect to the locking element 40. The curvature is at least the same over an overlapping surface which here is defined as the surface which encompasses the maximal gliding motion of the washer 41 on the contact surface 80.

In the present embodiment the first contact surface 80 has a convex shape, whereas the second contact surface 81 has a concave shape. Such a configuration is particularly advantageous as it allows a pivoting motion as mentioned above while providing a very compact structure of the fixation clamp in terms of axial and radial dimension. Furthermore the surfaces which are shaped as explained allow that the washer 41 as explained in detail below is removable from the clamping element 10. Thereby the first clamping assembly 20 and the second clamping assembly 30 become loose such that the parts are slightly moveable along middle axis M and sterilization of the clamping element 10 is possible without demounting the clamping element 10 completely. This is very advantageous since during sterilization the parts remain together and re-assembly of the parts afterwards is not necessary. Hence the parts of the clamping element 10 remain loosely together such that the sterilization fluid is able to enter clearances between the respective parts. As mentioned above providing the diameters D1 and D2 accordingly, the abutment surface 86 serves as element which holds the parts loosely together.

The first contact surface 80 of the first clamping assembly 20 extends from a section point 82 between the middle axis M of the locking element 40 and the first contact surface 80 towards the first clamping assembly 20.

FIG. 3 shows the clamping element from above. In FIG. 3 the overlapping surface with limiting edges 54 can be recognized.

Figure 4:
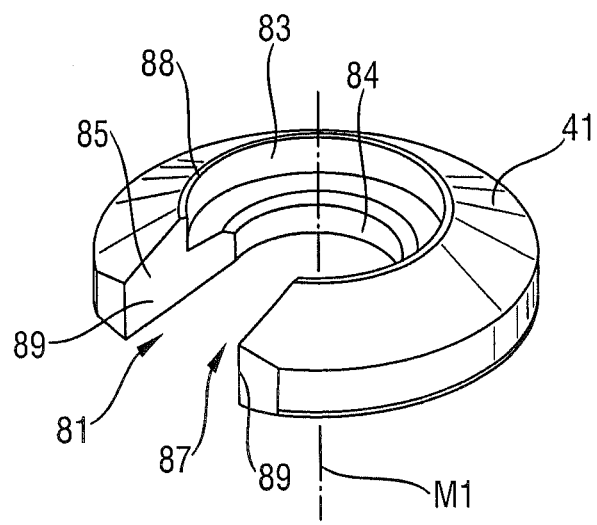
FIG. 4 shows a perspective view of a washer that is used in the fixation clamp of FIG. 1.

FIG. 4 shows the washer 41 in a perspective view and in FIG. 2 a cross-sectional view of the washer 41 is shown. In the following the structure of the washer 41 will be explained.

The washer 41 comprises as mentioned above the contact surface 81 and an upper surface 88 which is arranged at a distance from the contact surface 81. A central through opening 84 having a middle axis M1 that is at least partly circumvented by means of a sidewall 85. The through opening extends from contact surface 81 to the upper surface 88. The locking element 40 extends through the through opening.

The sidewall 85 is interrupted by a slot or cutout 87 which extends radially to the middle axis M1 through the sidewall to the opening 84 such that the sidewall 85 becomes interrupted. The cutout 87 has a width which is slightly larger than the reduced diameter portion 43 of the locking element 40 such that the washer 41 can be moved radially to the locking element 40 in order to remove the washer 41 after the use of the clamping element 10. The width is defined as the clearance of the cutout 87 from the surfaces 89 of the sidewall limiting the cutout.

Furthermore the washer 41 comprises a recess 83 extending along middle axis M1 from an upper surface 88 which is arranged opposite the contact surface 81. The recess 83 is designed to accommodate the flange 45 of the locking element 40. The recess 83 can also be designated as abutment element since it prevents that washer from being radially displaced to the middle axis M of the locking element 40. In order to demount or remove the washer 41 it is necessary to push the first clamping assembly 10 towards the second clamping assembly, such the washer 41 can also be moved along the middle axis M of the locking element 40. Thereby the flange 45 will be moved out of the recess 83. Once the flange 45 has been moved such that there is no connection between the flange 45 and the recess 83, the washer 41 can be moved radially to the locking element 40 whereby the shaft of the locking element will pass through the cutout 87 of the washer.

Recess 83 extends from the upper surface 88 along the middle axis M1 of the through opening 84 into the washer 41. The washer is preferably made out of a metallic material.

To summarize the arrangement of the contact surfaces 80, 81 has the advantage that during the mounting process of the fixation clamp 10 a pivoting motion of the first clamping assembly becomes possible with a large deflection. Furthermore the removable washer 41 has the advantage that the clamping assemblies 20, 30 become moveable along the interlocking element such that an effective sterilization becomes possible. The spring 15 may be sized in length so that it is placed under tension only when the washer is in place. Thus, when the washer is removed, there is no spring force of the components.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fixation clamp for use in an external fixation system for holding bone fragments adjacent to each other with the help of fixation elements, said fixation clamp comprising
   at least one clamping assembly having at least one reception adapted to accommodate a fixation element along a longitudinal axis of the reception and a first contact surface;
   at least one locking element extending along an axis through an opening in the at least one clamping assembly for blocking the position of the at least one clamping assembly in a defined angular position, the locking element having a head and a shaft, the locking element head having a diameter larger than a diameter of the shaft, and
   a washer which is arranged between said locking element head and said at least one clamping assembly, the washer has a through bore surrounded by a recess that receives the locking element head and an opening extending radially from the bore to an outer surface of the washer, the opening having a width greater than the locking element shaft diameter but less than the head diameter;
   wherein said washer comprises a second contact surface and wherein the second contact surface is in contact with said first contact surface; and
   wherein the at least one clamping assembly and the washer are slidable along the locking element shaft while the first and second contact surface are in contact at least until the locking element head is clear of a washer surface surrounding the recess, which surface is transverse to the locking element axis and opposite the second contact surface.

2. The fixation clamp according to claim 1, wherein said washer is dismountable from the locking element shaft by relative movement with respect to the shaft through the radially extending opening of the washer in a direction substantially perpendicular to said locking element axis.

3. The fixation clamp according to claim 1, wherein the washer outer surface comprises an outer wall and the through bore receiving the locking element and defining an inner side wall.

4. The fixation clamp according to claim 3, wherein said washer opening extends radially from the outer wall to the inner wall defined by said through bore such that said washer is mountable and demountable in substantial radial direction to the axis of the locking element.

5. The fixation clamp according to claim 1 wherein the first and second contact surfaces are part spherical.

6. The fixation clamp according to claim 5, wherein the first contact surface of the clamping assembly is convex and extends from the bore receiving the locking element towards the clamping assembly and the second contact surface is concave.

7. The fixation clamp according to claim 6, wherein a radius of curvature of the part-spherical convex and concave contact surfaces on the washer and clamp assembly is constant at least with respect to the overlapping surface between the first contact surface of the clamping assembly and the second contact surface of the washer.

8. The fixation clamp according to claim 6, wherein the clamping assembly first concave surface is complementary to the washer convex surface.

9. The fixation clamp according to claim 1, wherein the locking element head comprises a radially extending flange which is in contact with said washer and wherein the recess in the washer has an inner wall which at least partly accommodates said flange.

10. The fixation clamp according to claim 9, wherein said recess extends radially from a middle axis of the washer through bore towards the washer outer surface.

11. The fixation clamp according to claim 9, wherein the clamping assembly opening through which said locking element extends, comprises, at least in part, a diameter that is larger than the diameter of the locking element flange.

12. The fixation clamp according to claim 1, wherein parts of the clamping assembly are pivotable against the locking element.

13. The fixation clamp according to claim 1, wherein the clamping assembly opening comprises at least one conical section such that the clamping assembly is pivotable against the locking element.

14. The fixation clamp according to claim 1, wherein the opening in the clamping element comprises, towards the first contact surface, a first diameter which is adjoined by a second diameter, wherein the first diameter is larger than the second diameter such that between the first and the second diameter an abutment surface is provided, which abutment surface serves as abutment element for the locking element flange when the washer is removed.

15. The fixation clamp according to claim 1, wherein each clamping assembly comprises two jaws, wherein each jaw comprises a number of grooves to form said receptions with the corresponding jaw.

16. The fixation clamp according to claim 1, wherein between the clamping assembly a spring element is arranged providing a force along the locking element.

17. The fixation clamp according to claim 16, wherein spaced along the locking element, a first clamping assembly is followed by at least a second clamping assembly, wherein the locking element is in contact with the second clamping element by means of a thread and wherein locking element extends through the first clamping assembly wherein said spring provides an axial force onto the first clamping assembly which is pushed against such washer.

18. A fixation clamp for an external fixation system comprising:
- a clamping assembly comprises first and second jaws, each jaw having an opening for receiving a rod or pin, each jaw having a central bore, the first jaw comprising a first outer contact surface;
- a locking element extending along a central axis received within the bores of the first and second jaws, the locking element having a shaft end and a head portion adjacent the first outer contact surface of the first jaw; and
- a washer having a second outer contact surface mounted on the first outer contact surface of the first jaw between the outer surface and the head portion of the locking element, the washer having a central bore receiving the locking element shaft portion, a recess surrounding the central bore for receiving the head portion and a slot extending from the washer central bore to an outer edge of the washer,
- wherein the at least one clamping assembly and the washer are slidable along the locking element shaft while the first and second outer contact surfaces are in contact at least until the locking element head is clear of a washer surface transverse to the locking element axis and surrounding the recess, which surface is opposite the washer second outer contact surface.

19. The fixation clamp as set forth in claim 18 wherein the washer is removable from the clamping assembly by movement in a direction generally perpendicular to the locking element axis.

20. The fixation clamp as set forth in claim 19 wherein the slot has a width greater than a diameter of the locking element shaft.

21. The fixation clamp as set forth in claim 18 wherein the central bore of each jaw is larger than a diameter of the locking element shaft allowing the washer to rotate on the first outer contact surface of the first jaw.

* * * * *